US007712960B2

(12) United States Patent
Sanishvili et al.

(10) Patent No.: US 7,712,960 B2
(45) Date of Patent: May 11, 2010

(54) DEVICE FOR OPTIMIZATION OF EXPERIMENTAL PARAMETERS ON SYNCHROTRON BEAM LINES

(75) Inventors: Ruslan Sanishvili, Naperville, IL (US); Robert F. Fischetti, Plainfield, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 12/391,740

(22) Filed: Feb. 24, 2009

(65) Prior Publication Data

US 2010/0074413 A1 Mar. 25, 2010

Related U.S. Application Data

(60) Provisional application No. 61/031,416, filed on Feb. 26, 2008.

(51) Int. Cl.

*A61B 6/08* (2006.01)
*G01D 18/00* (2006.01)
*G21K 1/06* (2006.01)
*G01N 23/207* (2006.01)

(52) U.S. Cl. ......................... 378/205; 378/207; 378/84; 378/73

(58) Field of Classification Search .................. 378/73, 378/84, 71, 70, 79, 85, 205, 207; 250/336.1
See application file for complete search history.

(56) References Cited

U.S. PATENT DOCUMENTS

| | | | | |
|---|---|---|---|---|
| 5,056,129 | A | 10/1991 | Steinmeyer | |
| 5,387,795 | A | 2/1995 | Kuzay et al. | |
| 5,949,847 | A | 9/1999 | Terada et al. | |
| 6,453,006 | B1 | 9/2002 | Koppel et al. | |
| 6,596,994 | B1 * | 7/2003 | Alkire et al. | 250/336.1 |

* cited by examiner

*Primary Examiner*—Irakli Kiknadze
(74) *Attorney, Agent, or Firm*—Joan Pennington

(57) ABSTRACT

Enhanced methods and a device enabling a plurality of tools for implementing a plurality of procedures for the accurate alignment and calibration of multiple components of the experimental set up at a synchrotron beam line are provided. The device includes an alignment pin or needle for centering a sample rotation axis. The device includes a YAG crystal for visualization of the beam and beam alignment and a metal foil for transmission or fluorescence measurements used for the monochromator calibration. The same, or different foils, or powders, or polymers, can be used for obtaining powder rings for finding the direct beam coordinates, for centering the beamstop on the direct beam and for calibration of the sample-to-detector distance.

20 Claims, 2 Drawing Sheets

DEVICE FOR OPTIMIZATION OF EXPERIMENTAL PARAMETERS ON SYNCHROTRON BEAM LINES

This application claims the benefit of U.S. Provisional Application No. 61/031,416 filed on Feb. 26, 2008.

CONTRACTUAL ORIGIN OF THE INVENTION

The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

FIELD OF THE INVENTION

The present invention relates to a tool used for optimization of experimental parameters on synchrotron beam lines.

More specifically, this invention relates to a device having capability for implementing multiple procedures for the accurate alignment and calibration of multiple components of an experimental set up at a synchrotron beam line.

DESCRIPTION OF THE RELATED ART

On synchrotron beam lines there are a number of procedures that need to be performed in order to optimize experiments in general and data collection from macromolecular crystals in particular.

These procedures include:

1) Alignment of the sample rotation axis,

2) Visualization of the x-ray beam at the sample position for inspection of its quality and/or location, 3) Alignment of the x-ray beam with the sample position, 4) Proper calibration of the sample-to-detector distance especially for samples with large unit cells, 5) Proper calibration of the monochromator energy for experiments utilizing resonance effects near absorption edges, 6) Knowing precise coordinates of the direct beam (i.e. diffraction origin), especially for samples with large unit cells, and 7) Accurate centering of the beamstop.

Performing all or some of the above listed steps regularly would be beneficial for optimizing the experiment, which in turn would enhance the data quality, throughput and efficiency of a beamline. Usually, these steps are performed with separate tools, each of which has a single function. For example, there are alignment pins, x-ray visualization pins with a YAG crystal or a fluorescent "phosphor" on them, special mounts with metal foils for monochromator calibration, and the like.

Currently carrying out such optimization steps is arduous and time consuming, utilizing one alignment tool at a time. Because of this, some of the steps are often overlooked to save time and effort. For example, sample to detector distance calibration, beamstop centering and other useful steps may not be performed at all, or performed poorly. Some of the steps, for example, finding the diffraction origin, are performed with inferior and some times dangerous methods, which may damage expensive detectors, such as recording attenuated beam directly on the detector and finding the center of the recorded spot.

Principal objects of the present invention are to provide improved methods and a device enabling a plurality of procedures for implementing accurate alignment calibration of multiple components of the experimental set up at a synchrotron beam line.

Important aspects of the present invention are to provide such methods and device substantially without negative effect and that overcome some of the disadvantages of prior art arrangements.

SUMMARY OF THE INVENTION

In brief, enhanced methods and a device enabling a plurality of tools for implementing a plurality of procedures for the accurate alignment and calibration of multiple components of the experimental set up at a synchrotron beam line are provided. The device includes an alignment pin or needle for centering a sample rotation axis. The device includes a Yttrium Aluminum Garnet (YAG) crystal for visualization of the beam and beam alignment. The device includes a metal foil or foils for transmission or fluorescence measurements used for the monochromator calibration. The device includes a metal foil, a polymer or a powder for sample-to-detector distance calibration for finding the direct beam position and for centering the beamstop with powder diffraction. The device also includes provisions enabling further expansion of functionality.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

In accordance with features of the invention, a device or versatile pin is provided that is called a "VersaPin". The device or VersaPin combines each of the tools needed to perform the above-listed optimization steps. The device or VersaPin of the invention carries an alignment needle for centering a rotation axis; YAG crystal for visualization of the beam and its alignment; metal foils to produce a powder diffraction pattern which will be used for finding the exact position of the direct beam, for calibration of the detector distance and for centering the beamstop. The device also carries metal foil or foils for calibration of the monochromator. Since all needed tools are assembled on a rigid post with known dimensions, one-time alignment of one of them is sufficient for putting any other tool in the position by simply applying the pre-determined offsets. The assembly of the device or VersaPin is based on commercially available pins used for crystal mounting and is compatible with all beamlines handling such samples.

Figure 1:
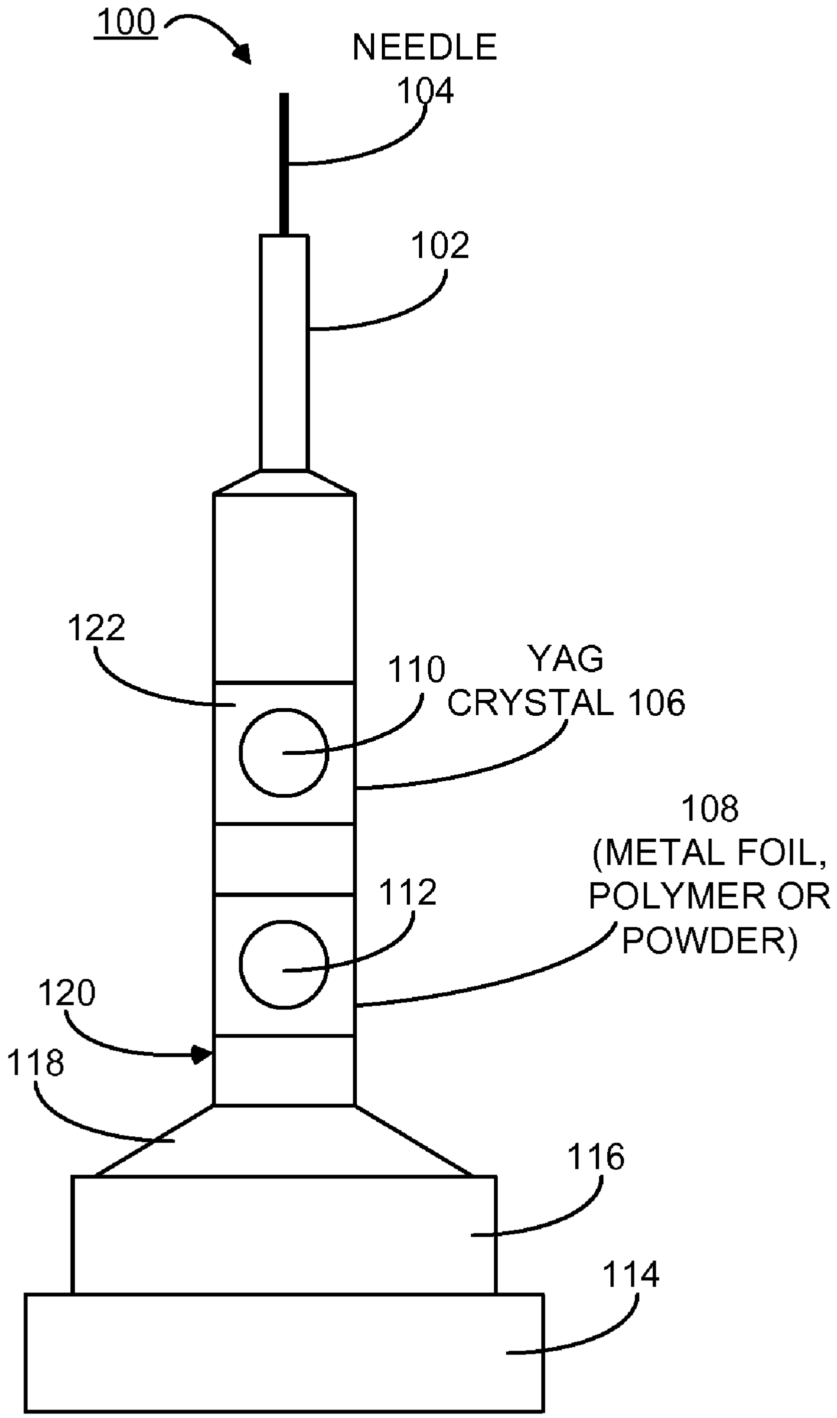
FIG. 1 is a front plan view of an exemplary device or versatile pin having capability for implementing multiple procedures for the accurate alignment and calibration of multiple components of the experimental set up at a synchrotron beam line in accordance with the preferred embodiment.
Figure 2:
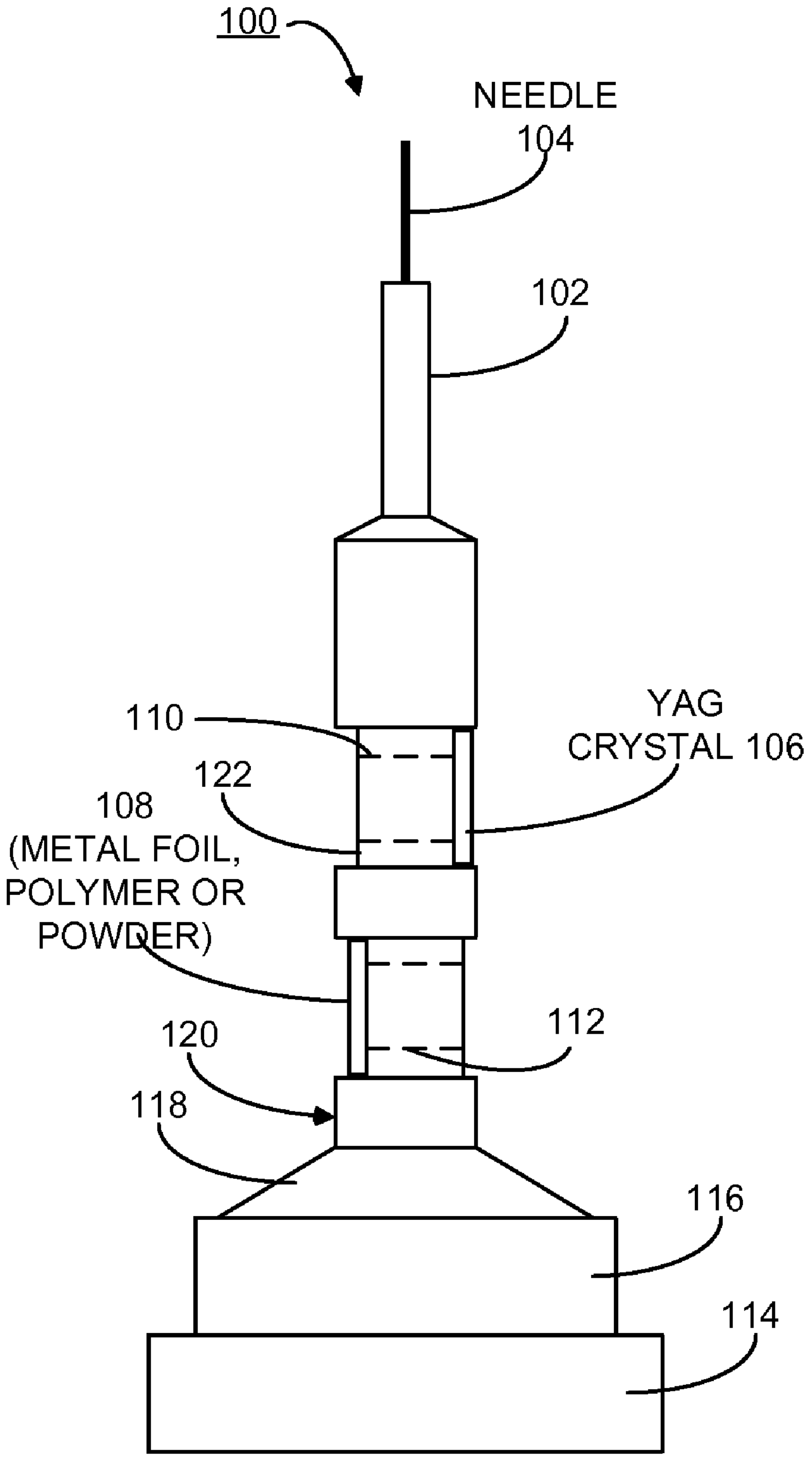
FIG. 2 is a side plan view of the exemplary device of FIG. 1 in accordance with the preferred embodiment.

Having reference now to the drawings, in FIGS. 1 and 2 there is shown an exemplary device having capability for implementing multiple procedures for the accurate alignment and calibration of multiple components of the experimental set up at a synchrotron beam line generally designated by the reference character 100 in accordance with the preferred embodiment.

Device 100 includes an alignment pin 102 for centering a sample rotation axis with a sample needle 104 disposed at an upper end of the device 100. Device 100 includes a YAG crystal 106 for visualization of the beam and its alignment and a metal foil 108 for transmission or fluorescence measurements used for the monochromator calibration; the same foil 108 can be used to produce powder rings for determining the exact direct beam position, for centering the beamstop and for calibrating the sample-to-detector distance. Device 100 includes a plurality of apertures or holes 110, 112, for example, respectively used for different extent of functionality with the YAG crystal 106, foils and, powders 108, as shown, and the like. Device 100 may include up to four holes similar to 110 and 112 for expanded functionality. For example, it may be equipped with a PIN diode (not shown) for intensity measurements and scanning.

All holes, for example holes 110, 112, are centered in slots 122 which are machined out from the post 120. This provides protection for the YAG crystal, foils, powders and polymers from mechanical damage by preventing accidental contact with them.

Device 100 includes a base 114, a spacer portion 116 disposed above the base 114, and a tapered portion 118 disposed above the spacer portion 116. The device 100 includes a post or member 120 supported by a tapered portion 118. Post 120 includes a plurality of slots 122.

The base 114, spacer portion 116, and tapered portion 118 may be formed as an integral unit, formed, for example, of a stainless steel material. The elongated member 120 is an integral member or rigid post mounted onto the tapered portion 116. All slots 122 and holes 110, 112 are machined with known dimensions. All needed tool features 102, 106, 108 are assembled in the slots 122 on the rigid post 120 with known dimensions, as a result, a one-time alignment of one of the tool features 102, 106, 108 is sufficient to allow the other tool features to be moved to the required position by simply applying the pre-determined offsets. The assembly defining the device 100 is based upon commercially available pins used for crystal mounting and is therefore compatible with all beamlines handling such samples, and is compatible for use with commercially available sample exchanger robotics.

In accordance with features of the invention, a plurality of new functions of the device 100 is provided to accomplish several tasks on synchrotron beamlines primarily. However, it should be understood that some of the functionality of device 100 can be used, for example, on experimental stations based on in-lab X-ray generators. This device 100, named VersaPin by the inventors, advantageously is made by modifying a commercially available, standard pin, for example, manufactured and sold by Hampton Research, or can be made from individually formed components and assembled together.

The device 100 or VersaPin advantageously is used for the following:

1. Centering the rotation axis on sample position
2. Visualizing of the X-ray beam for quick inspection of its quality
3. Alignment of the X-ray beam with the sample position
4. Obtaining the precise coordinates of the direct beam
5. Centering the beamstop on the direct beam
6. Calibrating the distance between the sample and the detector
7. Calibrating the monochromator at one or more energies The device 100 or VersaPin replaces at least four different prior art tools including: alignment pin; beam visualization mount (YAG, phosphor screen, scintillator and the like); mounted foils for transmission or fluorescence measurements used for the monochromator calibration; and another separate mount for obtaining powder rings.

In accordance with features of the invention, the device 100 or VersaPin only requires initial centering of the needle 102, which can be manual or automated. Then placement of all other positions is by simple translations by predetermined amounts, known from the specifications of the device 100 or VersaPin. Consequently, the device 100 or VersaPin enables a considerable savings of time.

In accordance with features of the invention, with the device 100 or VersaPin using powder diffraction for calibrating the detector distance and for finding the diffraction origin is much faster and more accurate than using other, more typically used methods, such as physical measurements of the distance, recording direct beam image and determining its center, using Bragg diffraction pattern from known crystal and the like.

In accordance with features of the invention, and probably most importantly, with the device 100 or VersaPin all alignments and calibrations described above can be automated relatively easily, due to the fact that the single, rigid device 100 is used for these steps. Such automation is being implemented on beamlines at Argonne National Laboratory and the procedures below are specific for this site.

Procedures for GM/CA Beamlines

Mount and Align the VersaPin

Mount device 100 on the goniometer head with omega=0°.

Drive the goniometer support outboard until the first slot 122 is roughly centered at the sample position, within the crosshairs of the high-resolution sample visualization camera.

Rotate device 100 on the magnetic base until YAG 106 is upstream or on the high resolution camera side, and is vertical; the low-resolution camera sees it “edge-on”.

Align the Rotation Axis

Move the VersaPin inboard with the goniometer support horizontal motion until the needle is visible in the field of view of the high-resolution camera.

With “point-and-click”, center the needle.

Increase the high-resolution camera zoom to maximum and center the needle.

Align the rotation axis by combining the goniometer support vertical and point-and-click motions, as needed.

Return omega to 0.

Visualize and Align the Beam

Move goniometer support horizontal 10 mm outboard.

Move the Crystal XY head X+1.03 mm.

Move Crystal XY Y+0.1 mm.

Search and close the hutch.

Open D shutter (B shutter on IDB line) and timing shutter.

Adjust the attenuation as needed.

Align the beam position as needed.

Direct Beam Coordinates, Beamstop and Sample-to-Detector Distance

Close the timing shutter and move goniometer support horizontal+3 mm to position the foil 108.

Record a diffraction image with 100× attenuation, 1 second exposure and 0.1° rotation width.

Match the movable circle in the MAR display software to the powder diffraction ring. The center of the ring is the center of direct beam.

Center the beamstop shadow on the center of the powder diffraction rings by iteratively moving the beamstop in the required direction or directions and taking diffraction images until the beamstop is centered.

Click anywhere on the first, lowest resolution, diffraction ring and write out the pixel address X and Y in mm.

Calculate D=SQRT((Xr−Xb)2+(Yr−Yb)2)/(Tan(2 arcsin (λ/2d)))+1.875 mm; where D is the sample-to-detector distance, Xr and Yr are the X and Y coordinates of any pixel in the ring, Xb and Yb are the X and Y coordinates of the direct beam (center of the diffraction rings), λ is the wavelength of the incident beam and d is the resolution or d-spacing (known) of the ring. The number 1.875 in this case is the distance from the position when YAG 106 is in focus to the foil 108. The resulting number is the true distance between the sample and the detector.

For more accurate measurement of the distance, multiple points can be chosen on the powder ring and the results averaged.

Monochromator Calibration

Start the monochromator calibration script.

If calibration at an additional energy is needed, move the goniometer support horizontal+3 mm to expose the additional foil (not shown) and start the calibration script.

The device 100 or VersaPin can be applied at various facilities, which differ by the range of their operational parameters such as the sample-to-detector distance, monochromator energy range, maximum beam intensity and the like. Facilities can also differ by functionality, for example, a fixed wavelength beamline. By choosing appropriate foils and powders device 100 or VersaPin can be designed to cover the widest range and most functionality of modern experimental stations ("one size fits all" approach). Alternatively, several types of devices 100 or VersaPins can be designed to address different ranges and functionalities separately (tailored approach), which can decrease the cost of the individual device.

While the present invention has been described with reference to the details of the embodiments of the invention shown in the drawing, these details are not intended to limit the scope of the invention as claimed in the appended claims.

What is claimed is:

1. A device for implementing a plurality of procedures for the accurate alignment and calibration of multiple components at a synchrotron beam line, said device comprising:

a post;

a plurality of holes in said post;

an alignment pin carried by said post for centering a sample rotation axis;

a Yttrium Aluminum Garnet (YAG) crystal coupled to said post for visualization of the beam and beam alignment; and a metal foil coupled to said post with predefined measurements used for a monochromator calibration, and enabling obtaining an accurate location of the direct beam, centering the beamstop on the direct beam and calibration of the sample-to-detector distance.

2. The device for implementing a plurality of procedures for the accurate alignment and calibration of multiple components as recited in claim 1 wherein said YAG crystal and said metal foil are mounted on opposite ends of the hole in said post.

3. The device for implementing a plurality of procedures for the accurate alignment and calibration of multiple components as recited in claim 1 wherein said YAG crystal is mounted on a same end of the hole in said elongated post as said metal foil.

4. The device for implementing a plurality of procedures for the accurate alignment and calibration of multiple components as recited in claim 1 includes at least one of a second metal foil, a polymer and a powder mounted at an end of a separate hole in said post.

5. The device for implementing a plurality of procedures for the accurate alignment and calibration of multiple components as recited in claim 1 includes at least one of a plurality of metal foils, a plurality of powders, and a plurality of polymers to produce a powder diffraction pattern used for calibration of a detector distance and for finding a position of the direct beam, and at least one metal foil for said monochromator calibration.

6. The device for implementing a plurality of procedures for the accurate alignment and calibration of multiple components as recited in claim 1 wherein said alignment pin, said YAG crystal and said metal foil are assembled with said post at predefined locations.

7. The device for implementing a plurality of procedures for the accurate alignment and calibration of multiple components as recited in claim 6 wherein predefined offsets are provided between each of said alignment pin, said YAG crystal and said metal foil.

8. The device for implementing a plurality of procedures for the accurate alignment and calibration of multiple components as recited in claim 1 wherein said elongated post includes a plurality of apertures.

9. The device for implementing a plurality of procedures for the accurate alignment and calibration of multiple components as recited in claim 8 wherein said YAG crystal and said metal foil are mounted on either side of one of said plurality of apertures.

10. The device for implementing a plurality of procedures for the accurate alignment and calibration of multiple components as recited in claim 1 includes a plurality of metal foils for calibration of said monochromator at different energies and for producing a powder diffraction pattern used for finding a position of the direct beam, centering the beamstop and calibration of a detector distance.

11. The device for implementing a plurality of procedures for the accurate alignment and calibration of multiple components as recited in claim 1 includes a slot and a hole for mounting a pin diode for beam intensity measurements.

12. The device for implementing a plurality of procedures for the accurate alignment and calibration of multiple components as recited in claim 1 includes a slot and a hole for mounting a specimen for centering at a sample position for aligning the beam with X-ray fluorescence.

13. A method for implementing a plurality of procedures with a device for the accurate alignment and calibration of multiple components at a synchrotron beam line comprising the steps of:

providing the device with a post and said post including a plurality of holes;

mounting an alignment needle onto said post, and using said alignment needle for centering a sample rotation axis;

mounting a Yttrium Aluminum Garnet (YAG) crystal at a first location on said post, and using said YAG crystal for visualization of the beam and beam alignment;

mounting a metal foil at a second location on said post, and using said metal foil for predefined transmission measurements and for a monochromator calibration.

14. The method for implementing a plurality of procedures with a device for the accurate alignment and calibration of multiple components as recited in claim 13 includes using a selected one of said metal foil, a different mounted metal foil, a powder, and a polymer for finding direct beam coordinates, for centering a beamstop on the beam and for accurately measuring sample-to-detector distance.

15. The method for implementing a plurality of procedures with a device for the accurate alignment and calibration of multiple components as recited in claim 13 includes using said metal foil for fluorescence measurements for a monochromator calibration.

16. The method for implementing a plurality of procedures with a device for the accurate alignment and calibration of multiple components as recited in claim 13 includes forming said plurality of holes in said post, and mounting said YAG crystal and mounting said metal foil adjacent to a respective one of said plurality of holes, and wherein predefined offsets are provided between each of said alignment pin, said YAG crystal and said metal foil.

17. The method for implementing a plurality of procedures with a device for the accurate alignment and calibration of multiple components as recited in claim 13 includes mounting a plurality of said metal foils to produce a powder diffraction pattern used for calibration of a detector distance and for finding a position of the direct beam, and at least one of said metal foils used for said monochromator calibration.

18. The method for implementing a plurality of procedures with a device for the accurate alignment and calibration of multiple components as recited in claim 13 includes providing a separate mount for a selected one of said metal foil, a polymer or a powder.

19. The method for implementing a plurality of procedures with a device for the accurate alignment and calibration of multiple components as recited in claim 13 includes using a predefined algorithm for implementation of procedures for one or a combination of procedures including centering the sample rotation axis, visualizing the beam, aligning the beam, obtaining a powder diffraction ring pattern, obtaining direct beam coordinates, centering the beamstop on the direct beam, calibrating a sample-to-detector distance, and calibrating the monochromator.

20. The method for implementing a plurality of procedures with a device for the accurate alignment and calibration of multiple components as recited in claim 19 wherein said predefined algorithm is tailored for a site.

* * * * *